United States Patent
Schanke et al.

(10) Patent No.: US 6,696,501 B2
(45) Date of Patent: Feb. 24, 2004

(54) OPTIMUM INTEGRATION OF FISCHER-TROPSCH SYNTHESIS AND SYNGAS PRODUCTION

(75) Inventors: Dag Schanke, Trondheim (NO); Roger Hansen, Trondheim (NO); Jostein Sogge, Stjørdal (NO); Karina Heitnes Hofstad, Ranheim (NO); Margrete H. Wesenberg, Trondheim (NO); Erling Rytter, Trondheim (NO)

(73) Assignee: Statoil ASA, Stavanger (NO)

( * ) Notice: Subject to any disclaimer, the term of this patent is extended or adjusted under 35 U.S.C. 154(b) by 0 days.

(21) Appl. No.: 10/149,060
(22) PCT Filed: Dec. 1, 2000
(86) PCT No.: PCT/NO00/00404
§ 371 (c)(1), (2), (4) Date: Sep. 19, 2002
(87) PCT Pub. No.: WO01/42175
PCT Pub. Date: Jun. 14, 2001

(65) Prior Publication Data
US 2003/0134911 A1 Jul. 17, 2003

(30) Foreign Application Priority Data
Dec. 9, 1999 (NO) .......................................... 19996091

(51) Int. Cl.[7] .............................................. C07C 27/00
(52) U.S. Cl. ...................... 518/705; 518/700; 518/702; 518/703; 518/704
(58) Field of Search ................................ 518/705, 702, 518/703, 704, 700

(56) References Cited

FOREIGN PATENT DOCUMENTS

| EP | 0516441 A1 | 12/1992 |
|---|---|---|
| GB | 2223029 A | 3/1990 |

*Primary Examiner*—J. Parsa
(74) *Attorney, Agent, or Firm*—Kirkpatrick & Lockhart LLP

(57) ABSTRACT

A method is described for conversion of natural gas or other fossil fuels to higher hydrocarbons, comprising the following steps: a) reaction of natural gas with steam and oxygenic gas in at least one reforming zone in order to produce a synthesis gas consisting primarily of hydrogen and CO, in addition to some carbon dioxide; b) passing said synthesis gas to a Fisher-Tropsch reactor in order to produce a crude synthesis stream consisting of lower hydrocarbons, water and non-converted synthesis gas; c) separation of said crude synthesis stream in a recovery zone, into a crude product stream mainly containing heavier hydrocarbons, a water stream and a tail gas stream mainly containing the remaining constituents; which is charaterized in that the method also comprises the following steps; d) stream reformation of at least part of the tail gas in a separate steam reformer; e) introduction of the reformed tail gas into the gas stream before this is led into the Fischer-Tropsch reactor.

20 Claims, 3 Drawing Sheets

OPTIMUM INTEGRATION OF FISCHER-TROPSCH SYNTHESIS AND SYNGAS PRODUCTION

CROSS REFERENCE TO RELATED APPLICATIONS

This application is based on international application No. PCT/NO00/00404, filed Dec. 1, 2000, having an International Publication Number of WO 01/42175 A1 and an International Publication Date of Jun. 14, 2001, which is based on Norwegian Patent Application No. 19996091, filed Dec. 9, 1999.

FIELD OF THE INVENTION

The present invention regards a system for chemical conversion of natural gas or another suitable fossil fuel to synthetic hydrocarbons (syncrude). In particular, the present invention regards a system for optimising the production of synthetic hydrocarbons.

DESCRIPTION OF THE INVENTION BACKGROUND

Known processes for conversion of natural gas or other fossil fuels to synthetic hydrocarbons comprise two steps. First, the natural gas or other fossil fuel is converted to synthesis gas, i.e. a mixture consisting predominantly of hydrogen and carbon monoxide, as well as some $CO_2$, which in a second step is converted to synthetic hydrocarbons through the so-called Fischer-Tropsch (FT) synthesis. The synthetic hydrocarbon product normally consists of higher hydrocarbons, i.e. pentane and higher compounds ($C_{5+}$). The process may also include an additional step in which the synthetic hydrocarbon crude product is upgraded to final products.

Synthesis gas for production of synthetic hydrocarbons is normally produced by steam reforming or partial combustion, or a combination of these two reactions. The water gas shift reaction also plays an important part in the production of synthesis gas. These reactions may be written as follows:

| 1) | steam reforming | $CH_4 + H_2O = CO + 3H_2$ | $\Delta H = 206$ kJ/mole |
|---|---|---|---|
| 2) | partial combustion | $CH_4 + \tfrac{1}{2}O_2 = CO + 2H_2O$ | $\Delta H = -519$ kJ/mole |
| 3) | water gas shift | $CO + H_2O = CO_2 + H_2$ | $\Delta H = -41$ kJ/mole |

The Fischer-Tropsch synthesis for producing synthetic hydrocarbons may be written as follows:

| 4) | FT synthesis | $CO + 2H_2 = [-CH_2-] + H_2O$ | $\Delta H = -167$ kJ/mole |
|---|---|---|---| where $[-CH_2-]$ is the basic building block for the hydrocarbon molecules. The FT synthesis is highly exothermic, which leads to heat transfer being a significant factor in the design of an FT reactor.

An important parameter for determining the theoretical maximum yield of synthetic hydrocarbons is the stochiometric number SN, defined as:

$$SN = (H_2 - CO_2)/(CO + CO_2) \quad 5)$$

Theoretically, the yield of synthetic hydrocarbons is at its highest when SN=2.0 and CO does not react further to form $CO_2$ via the water gas shift reaction (equation 3). In this case, the $H_2/CO$ ratio will be equal to SN, i.e. 2.0, which theoretically gives the highest yield of synthetic hydrocarbons in accordance with equation 4. In practice however, the production of synthesis gas will always involve the water gas shift reaction to a certain degree, so that the CO yield, and thus also the synthetic hydrocarbon yield, becomes somewhat lower.

Further, the maximum yield of synthetic hydrocarbons is in reality achieved at a somewhat lower $H_2/CO$ ratio, typically around 1.6–1.8. At an $H_2/CO$ ratio of 2.0 or more, the synthetic hydrocarbon yield will be reduced due to the formation of more methane and other lower hydrocarbons ($C_{4-}$), which are normally undesirable products.

The preferred technology for producing synthetic hydrocarbons from synthesis gas is non-catalytic partial oxidation (POX) or autothermal reforming (ATR), in which partial combustion is combined with adiabatic catalytic steam reforming (equation 1) in the same reactor unit.

Another technology is combined reforming with a tubular catalytic steam reformer followed by an ATR.

A desired $H_2/CO$ ratio is achieved by running the synthesis gas reactor with a combination of a low steam/carbon ratio (S/C) and a high temperature, in addition to recirculating part of the $CO_2$-rich tail gas from the FT synthesis to the synthesis gas reactor in order to limit the water gas shift activity (equation 3). In this manner, the $H_2/CO$ ratio will approach the achieved value of SN.

The drawback of the known techniques for producing synthetic hydrocarbons is low carbon efficiency in comparison with the theoretical achievement. The carbon efficiency is defined as the relationship between the total amount of carbon in the produced crude product of synthetic hydrocarbons and the total amount of carbon in the natural gas feed. As such, the carbon efficiency is a measure of how much of the carbon in the feed actually ends up in the final product, and how much ends up as $CO_2$. A plant with low carbon efficiency gives a low product yield, a large $CO_2$ emission and thus an environmental problem.

As mentioned, catalytic autothermal reforming (ATR) and non-catalytic partial oxidation (POX) are the preferred technologies for production of synthesis gas for the FT synthesis. By using natural gas as a feed, these technologies produce a synthesis gas with an SN value typically in the range 1.6 to 1.8, which gives the highest yield of synthetic hydrocarbons locally in the FT reactor. However the SN value is lower than 2.0, which for the plant as a whole implies a lower carbon efficiency than that which may theoretically be achieved, due to a hydrogen deficiency.

Combined reforming, which normally takes place in a tubular catalytic steam reformer followed by a secondary reformer with an oxygen feed, is capable of producing synthesis gas with an SN value of 2.0, which should theoretically give the highest carbon efficiency in the plant for production of synthetic hydrocarbons. The real carbon efficiency will however not be higher than that which is achieved by use of POX or ATR, due to the higher degree of recirculation of tail gas to the synthesis reaction that is required in order to restrict a greater water gas shift activity than in the ATR as a result of the higher S/C ratio, and due to a lower yield of the desired higher synthetic hydrocarbons at this SN value.

It is thus an object of the present invention to provide an improved method for conversion of natural gas or other fossil fuels to higher hydrocarbons, in which the above mentioned drawbacks of the known techniques have been overcome.

SUMMARY OF INVENTION

According to the present invention, this is achieved by a method for conversion of natural gas or other fossil fuels to higher hydrocarbons, which comprises the steps of:

a) reacting natural gas with steam and oxygenic gas in at least one reforming zone in order to produce a synthesis gas that consists primarily of $H_2$ and CO, in addition to some $CO_2$;

b) lead said synthesis gas to a Fischer-Tropsch reactor in order to produce a crude synthesis stream consisting of lower hydrocarbons, higher hydrocarbons, water, and unconverted synthesis gas;

c) separating said crude synthesis stream in a recovery zone, into a crude product stream that primarily contains lower hydrocarbons, higher hydrocarbons, a water stream and a tail gas stream that mainly contains the remaining constituents; characterised in that the method also comprises the steps of;

d) steam reforming at least part of the tail gas in a separate steam reformer;

e) introducing the reformed tail gas into the gas stream before this is fed into the Fischer-Tropsch reactor.

"Lower hydrocarbons" refers to $C_1$–$C_4$ hydrocarbons. "Higher hydrocarbons" refers to $C_{5+}$ hydrocarbons.

It is preferable for the steam reforming in step d) to take place at conditions that favour the conversion of $CO_2$ to CO by reversible water gas shift reaction.

Moreover, it is preferable to also hydrogenate that part of the tail gas that is steam reformed, in order to saturate any unsaturated hydrocarbons prior to step d).

In a preferred embodiment, natural gas is fed to the steam reformer in step d) together with the tail gas feed.

In a preferred embodiment, the reformed tail gas is introduced into the gas stream after step a), but before step b).

In another preferred embodiment, the reformed tail gas is introduced into the gas stream before step a).

It is also preferred that part of the reformed tail gas be introduced into the gas stream before step a) and part of it be introduced after step a) but before step b).

Use of the present method has several advantages over previously known techniques.

By reforming and recirculating the tail gas, it becomes possible to:

Increase the SN value from typically 1.6–1.8 for an ATR to approximately 2.0.

Maintain or increase the CO yield, so that the $H_2$/CO ratio approaches the SN value.

Achieve an $H_2$/CO ratio of less than 2.0 locally at the inlet to the FT reactor, which gives a higher yield of higher hydrocarbons.

The present method results in higher carbon efficiency and higher thermal efficiency. This gives a desired reduction in the $CO_2$ emission, which is desirable, both for environmental and economic reasons. The oxygen consumption by the present method is lower than in the case of conventional plants for production of synthesis gas by use of POX or ATR, which entails reduced capital costs and lower power consumption.

It is also possible to achieve operational benefits such as increased stability by the oxygen fired synthesis gas reactor operating at a somewhat lower output temperature than that which is the case when using previously known technology. The increased methane content (lower conversion of natural gas) caused by this will be reformed in the tail gas reformer.

By eliminating the recirculation of tail gas to the main section for synthesis gas, it is also possible to economise with regard to the size of the equipment, and thereby to save costs in this section.

BRIEF DESCRIPTION OF THE DRAWINGS

The invention will now be explained in greater detail with reference to the accompanying drawings, in which.

DETAILED DESCRIPTION OF THE PREFERRED EMBODIMENTS

Figure 1:
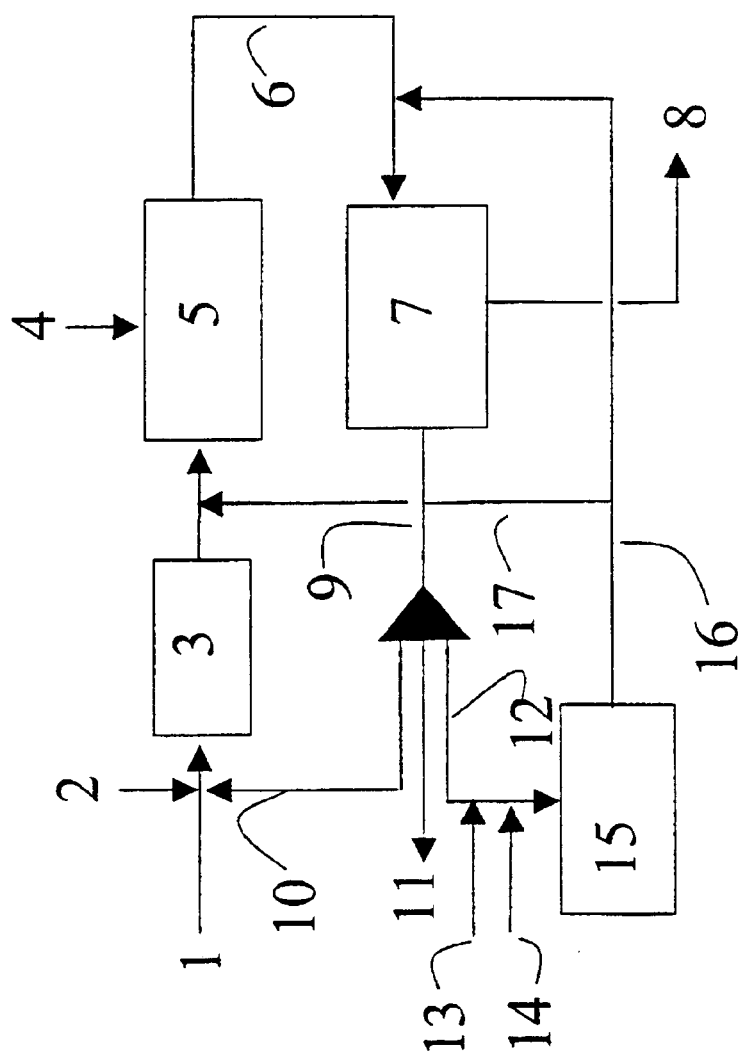
FIG. 1 is a simplified flow diagram showing the process for producing synthetic hydrocarbons by the present method.
Figure 2:
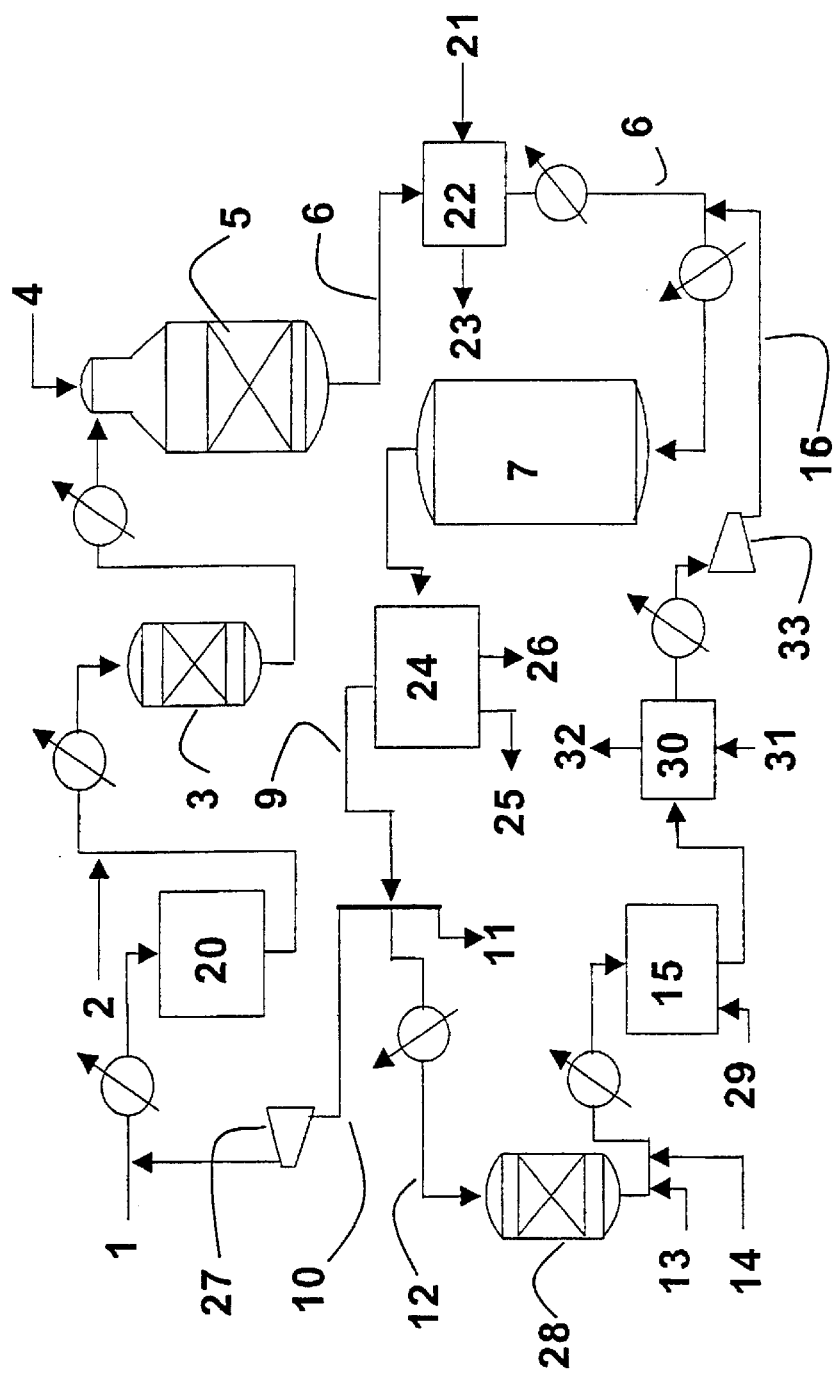
FIG. 2 is a more detailed flow diagram showing a first preferred embodiment of the present method.
Figure 3:
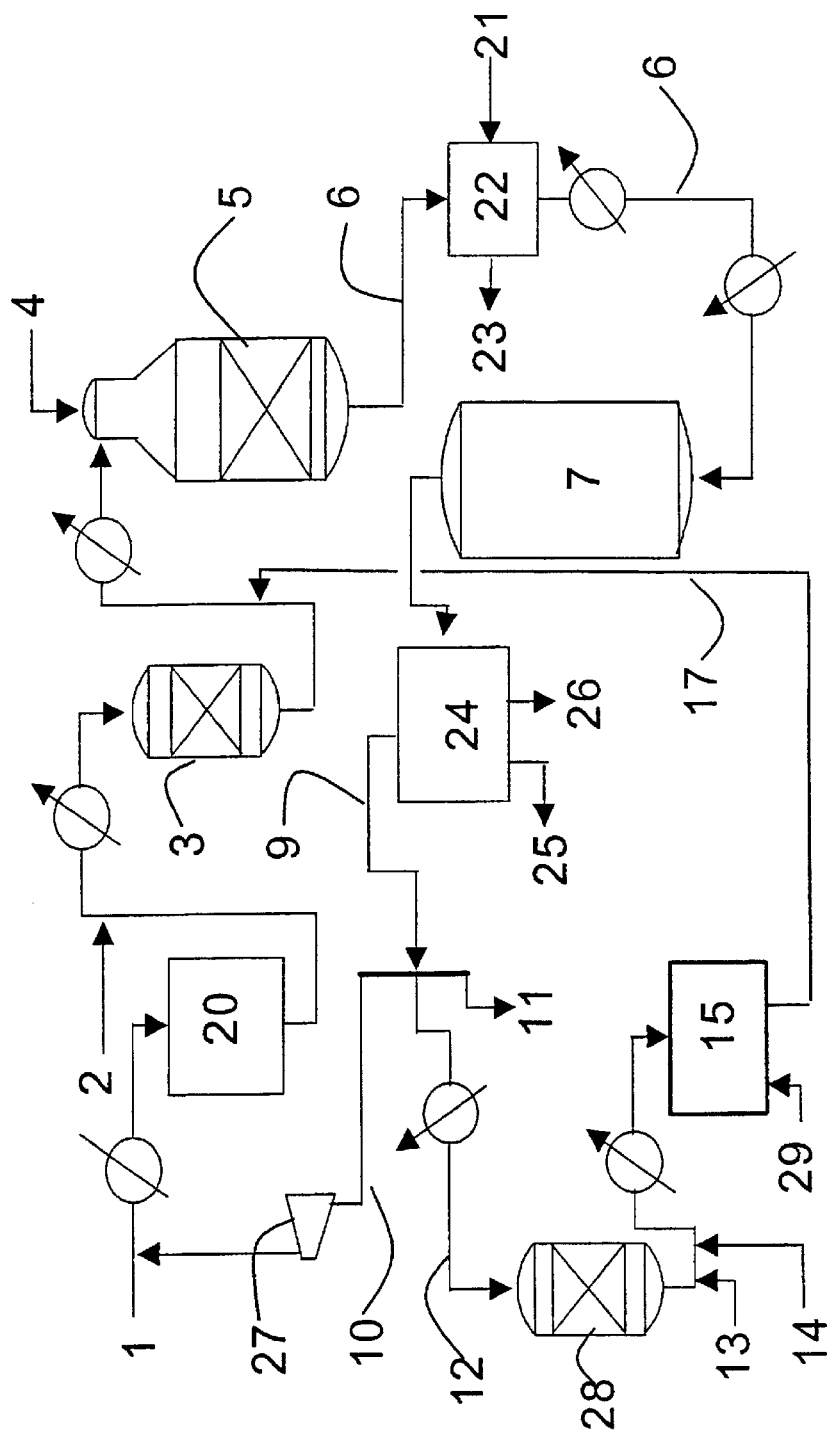
FIG. 3 is a more detailed flow diagram showing a second preferred embodiment of the present method.

The simplified flow diagram in FIG. 1 shows a method for producing synthetic hydrocarbons by using natural gas as the main source of carbon and hydrogen, while FIGS. 2 and 3 represent more detailed flow diagrams showing two preferred versions of this method.

The present method of FT synthesis based on natural gas or other fossil fuels may be divided into three main parts; that is a first part for production of synthesis gas, a second part for Fischer-Tropsch synthesis (FT synthesis) and a third part for reforming tail gas from the FT synthesis.

Production of Synthesis Gas

Natural gas enters the plant primarily through natural gas line 1. The natural gas is first heated to typically about 350–400° C. before being passed through a desulphurization unit 20. Here sulphur, which is present in the natural gas in the form of various organic compounds, is converted to hydrogen sulphide through contacting it with an appropriate hydrogenation catalyst. The hydrogen sulphide is then reduced to a desirable level by use of a zinc oxide layer.

After desulphurization, water vapour is added to the gas in order to ensure a desired ratio between water vapour and carbon (S/C ratio), typically from about 0.6 to 1.3 for production of synthetic hydrocarbons. The gas/water vapour mixture is preheated and introduced into a prereformer 3 that converts $C_2$ and higher hydrocarbons to $CH_4$, CO and $CO_2$. The operating temperature in the prereformer 3 is typically in the range 430 to 500° C. The prereformer may be omitted, in particular when using natural gas with a low content of $C_{2+}$.

Hydrogen, which is required in the desulphurization unit 20 and in the prereformer 3, is added to the natural gas before it enters the desulphurization unit 20. As indicated in the figures, part of the tail gas containing amongst other things hydrogen, may be recirculated and added to the gas before it enters the desulphurization unit 20. It is also possible to recover hydrogen from said tail gas by e.g. pressure swing adsorption (PSA), or hydrogen may be supplied from another source.

The preformed gas mixture is then heated further to a temperature of typically 550–650° C., before being sent into an autothermal reformer (ATR) 5 together with oxygen or an oxygenic gas such as e.g. air, which comes in through an oxygen inlet 4, normally from a cryogenic oxygen plant (not shown). The gas that is fed to ATR 5 is converted to synthesis gas in ATR 5 through partial combustion in the upper part of ATR 5 and steam reforming of the gases across a nickel catalyst in the lower section of ATR 5. The formation of synthesis gas in ATR 5 typically takes place at a pressure of about 30–40 bar, and the outlet temperature of the gas from ATR 5 is typically in the range 950–1050° C.

The hot synthesis gas leaving ATR 5 in synthesis gas line 6 is first cooled in a heat exchanger 22, in which typically water from inlet 21 is converted to high pressure steam in outlet 23. One heat exchanger has been indicated in the figures, however in practice there may be a plurality of heat exchangers connected in series, cooling the synthesis gas to the desired temperature. The last cooling down to typically 40–70° C. is achieved by use of cooling water.

Condensed water is then separated out from the synthesis gas before this is led to a Fischer-Tropsch synthesis reactor 7.

Fischer-Tropsch Synthesis

The desired synthetic hydrocarbons are formed in a known manner in a Fischer-Tropsch reactor (FT reactor) 7 in which hydrogen and carbon monoxide are converted to higher hydrocarbons, leaving water as a by-product, according to equation (4) above. The FT reactor 7 is typically run at 20–40 bar pressure and a temperature of 180–240° C. As the reaction is exothermic, heat is normally removed from the reactor 7 through generation of water vapour at an intermediate pressure of typically around 5–20 bar.

The product streams from the FT reactor 7 typically contain the desired product in the form of $C_{5+}$ hydrocarbons, by-products in the form of lower hydrocarbons ($C_{5-}$), $CO_2$ and water, as well as non-reacted synthesis gas, i.e. CO and hydrogen. This product stream is separated in a product recovery unit 24, into a crude product stream containing primarily the desired hydrocarbon product in outlet 25, separated water in outlet 26 and a tail gas stream chiefly comprising the above by-products and non-reacted synthesis gas, in tail gas line 9.

The tail gas in tail gas line 9 is in turn split into three. A first part goes through recirculation line 10 and is compressed in a compressor 27 for recirculation to the synthesis gas production as indicated below, a second part goes through a reforming line 12 to a tail gas reforming process, while a third part is drawn off through bleed line 11 and, if so required, used as fuel in heat consuming parts of the process.

Tail Gas Reforming

The tail gas in tail gas line 12 is preferably first led to a tail gas hydrogenator 28 in order to saturate any unsaturated hydrocarbons. The operating temperature of the hydrogenator 28 is typically 220–250° C., while the operating pressure is around 20–40 bar. This tail gas hydrogenator 28 is not obligatory preferred, however unsaturated hydrocarbons have a greater tendency towards coking than saturated hydrocarbons during the subsequent high temperature treatment.

After the tail gas hydrogenator 28, water vapour and possibly an amount of natural gas are added to the tail gas in vapour inlet 13 and gas inlet 14 respectively, before the gas is preheated and passed into a tail gas reformer 15 in which light hydrocarbons are steam reformed on formation of CO and hydrogen, cf. equation 1) above, while $CO_2$ present in the tail gas is converted to CO through a reverse water gas shift reaction according to equation 3). The natural gas feed can be taken from the product stream from the prereformer 3 (clean split).

The operating temperature of the tail gas reformer is typically above 800° C., preferably from 850 to 950° C., while the operating pressure is normally from 10 to 40 bar. If so necessitated by the operating pressure difference between the tail gas reformer and the FT reactor, a compressor may be provided downstream of the tail gas reformer. Energy for these reactions can be provided by combustion of fuel that may consist of a small part of the tail gas from bleed line 11.

Depending on the $C^{2+}$ content of the gas that may be added in gas inlet 14, it may become necessary to install a prereformer after the addition of water vapour, upstream of the tail gas reformer. The purpose of such a prereformer, which is of the same type as the prereformer 3, is to convert ethane and higher hydrocarbons in the gas stream to methane, CO and $CO_2$, thereby to avoid/reduce coking at high temperatures. If no natural gas is added in inlet 14, or when using natural gas with a methane content of 90% or more, there will normally not be a requirement for a prereformer here.

The hot flow of reformed tail gas from the tail gas reformer 15 can then be cooled in a heat exchanger 30 in which water that comes in through inlet 31 is converted to water vapour that exits through vapour outlet 32. One heat exchanger has been indicated in the figures, however in practice there may be a plurality of heat exchangers connected in series, cooling the synthesis gas to the desired temperature. Condensed water is then separated out from the reformed tail gas before this is compressed in compressor 33 and led through tail gas line 16 to synthesis gas line 6 before this enters the FT reactor. It is also possible to introduce the reformed tail gas directly into the gas stream between the prereformer 3 and the autothermal reformer (ATR) 5. In addition it will be possible to split the flow of reformed tail gas and lead one component stream to the FT reactor 7 and one component stream to ATR 5.

The purpose of leading the reformed tail gas to ATR 5 is to achieve further steam reforming and the formation of CO through the reversible water gas shift reaction, as the temperature of ATR 5 is higher than that of the tail gas reformer, thus attaining a higher carbon efficiency for the plant. This effect may be partially countered through combustion of CO and hydrogen to $CO_2$ and water. The choice of solution here, and any decision regarding how much of the reformed tail gas goes where, will depend on a number of operational parameters.

The primary purpose of reforming and recirculating tail gas according to the present invention is to steam reform lower hydrocarbons to CO and hydrogen, thereby to increase the stochiometric number SN towards the desired value of 2.0, which is an important condition for achieving a significantly higher efficiency for the process plant. As the tail gas contains little in the way of light hydrocarbons, steam reforming of this stream alone will only give a limited increase in efficiency. Adding natural gas or another source of lower hydrocarbons through gas inlet 14 will therefore give a further increase in carbon efficiency.

Another advantage of adding natural gas to the tail gas reformer is to reduce the amount of feed gas to ATR 5, which gives a lower oxygen consumption than that of a conventional synthesis plant with ATR.

The Overall System

In total, the present method gives a noticeable and important increase in the carbon efficiency, a reduction of the oxygen consumption and improved overall economy for the plant.

By reforming and recirculating a significant portion of the tail gas to the FT reactor 7 and/or ATR 5, the equipment in the feed section to the ATR unit can be smaller than that which would be the case if the tail gas were to be recirculated to the hydrogenation unit 28, as is common today.

The tail gas from the product recovery section 24 is, as mentioned above, split into three parts. It has proven advantageous to recirculate 0–20%, for example around 10%, to the hydrogenation unit 28; use 0–40%, for example around 30% as fuel in the tail gas reformer; and use 40–80%, for example around 60%, as feed to the tail gas reforming part of the process.

EXAMPLE

Five different plants/modes of operation of the plant were simulated in order to show the advantages of the present invention compared with previously known technology traditionally used in plants for synthesis of synthetic hydrocarbons. In all the examples, the production was set at 20 000 BPD or 101 tons/hour. The examples were as follows:

Ex. A Production of synthetic hydrocarbons by conventional autothermal reforming (ATR).

Ex. B Production of synthetic hydrocarbons by conventional combined reforming.

Ex. C Production of synthetic hydrocarbons by ATR and F-T tail gas reformer. No addition of natural gas to the tail gas reformer. The product from the tail gas reformer was fed to the F-T reactor.

Ex. D Production of synthetic hydrocarbons by ATR and F-T tail gas reformer. 10% of the natural gas feed to the process is added directly to the tail gas reformer. The product from the tail gas reformer was fed to the F-T reactor. The portion of the tail gas that is drawn off from the plant is used as fuel gas in the tail gas reformer.

Ex. E Production of synthetic hydrocarbons by ATR and F-T tail gas reformer. 20% of the natural gas feed to the process is added directly to the tail gas reformer. The product from the tail gas reformer was fed to ATR. 3% of the total natural gas feed is used as fuel in the tail gas reformer together with the portion of the tail gas that is drawn off from the plant.

The crude product was natural gas with the following composition:

| | |
|---|---|
| $CO_2$ | 1.84% |
| $N_2$ | 0.36% |
| $CH_4$ | 80.89% |
| $C_2H_6$ | 9.38% |
| $C_3H_8$ | 4.40% |
| $C_4H_{10}$ | 2.18% |
| $C_5H_{12}$ | 0.62% |
| $C_6H_{14}$ | 0.22% |
| $C_8H_{18}$ | 0.11% |

These simulations gave the following results as to the most important key data:

| | Ex. A Compar. ex. | Ex. B Compar. ex. | Ex. C | Ex. D | Ex. E |
|---|---|---|---|---|---|
| Natural gas feed, kmol/h | 7767 | 7790 | 7150 | 7062 | 7070 |
| S/C, synthesis gas line | 0.6 | 1.8 | 0.6 | 0.6 | 0.6 |
| Oxygen consumption, ton/day | 4590 | 3289 | 3801 | 3399 | 3290 |
| Fischer-Tropsch tail gas used as fuel gas, % of total tail gas | 40 | 25 | 30 | 30 | 30 |

-continued

| | Ex. A Compar. ex. | Ex. B Compar. ex. | Ex. C | Ex. D | Ex. E |
|---|---|---|---|---|---|
| Fischer-Tropsch tail gas added to ATR, % of total tail gas | 60 | 75 | 9 | 9 | 9 |
| Fischer-Tropsch tail gas added to tail gas reformer, % of total tail gas | — | — | 61 | 61 | 61 |
| S/C[3] tail gas reformer | — | — | 5.3 | 1.0 | 0.6 |
| $CO_2$/C[3] tail gas reformer | — | — | 5.3 | 1.0 | 0.6 |
| Outlet temperature tail gas reformer, °C. | — | — | 900 | 900 | 900 |
| Carbon efficiency, %[1] | 71.0 | 70.9 | 77.1 | 78.0 | 77.9 |
| Thermal efficiency, %[2] | 59.4 | 59.2 | 64.6 | 65.3 | 65.3 |
| $CO_2$ emission, ton/h | 127.11 | 128.39 | 92.50 | 87.46 | 88.00 |

[1]Carbon efficiency = amount of carbon in the synthetic crude product/total amount of carbon in the natural gas feed
[2]Thermal efficiency = lower thermal value (i.e. the thermal value obtained by complete combustion) in the synthetic crude product/lower thermal value in total natural gas feed
[3]Organic carbon The above table clearly shows the advantages of using the present method (ex. C, D and E) in preference to the previously known methods (ex. A and B).

For the same quantity of product, the present method reduces the consumption of natural gas by around 8–10%, which in turn is directly reflected by the carbon efficiency and the thermal efficiency, which for the present method are significantly higher than when using the previously known methods.

Another significant effect, which is clearly associated with the above results, is that of the considerable reduction in $CO_2$ emissions for the same produced quantity of synthetic hydrocarbons. As can be seen from the above table, the $CO_2$ emissions by use of the present method are around 40% lower than those caused by use of conventional methods.

The oxygen consumption in example B, which is a method according to prior art, was the lowest among the simulated examples. Although low oxygen consumption is positive, the results for the critical parameters, i.e. carbon efficiency and thermal efficiency, are significantly poorer than in the case of the present invention, i.e. examples C, D and E.

The above invention has been described as using natural gas as the source of carbon. The process may however be used for all types of gas that contain large amounts of lower hydrocarbons, as well as for other fossil fuels and possibly combinations of various carbon sources.

What is claimed is:

1. A method of converting natural gas or other fossil fuels to higher hydrocarbons, comprising:
   reacting the natural gas or the other fossil fuels with steam and oxygenic gas in at least one reforming zone to produce a synthesis gas containing primarily $H_2$ and CO, and an amount of $CO_2$;
   passing the synthesis gas to a Fischer-Tropsch reactor to produce a crude synthesis stream containing lower hydrocarbons, water and non-converted synthesis gas;

separating the crude synthesis stream in a recovery zone, into a crude product stream mainly containing lower hydrocarbons, higher hydrocarbons, a water stream and a tail gas stream containing the remaining constituents;

steam reforming at least a portion of the tail gas in a separate steam reformer and introducing the reformed tail gas into the gas stream before being fed into the Fischer-Tropsch reacter.

2. The method according to claim 1, wherein the temperature during the steam reforming is above 800° C.

3. The method according to claim 2, wherein the temperature during the stream reforming is in the range of 850° C. to 950° C.

4. The method according to claim 1, wherein the portion of the tail gas that is steam reformed is hydrogenated in order to saturate any unsaturated hydrocarbons prior to the stream reforming.

5. The method according to claim 2, wherein the portion of the tail gas that is steam reformed is hydrogenated in order to saturate any unsaturated hydrocarbons prior to the stream reforming.

6. The method according to claim 1, wherein the natural gas or other fossil fuels is added to the steam reformer together with the tail gas feed for steam reforming.

7. The method according to claim 2, wherein the natural gas or other fossil fuels is added to the steam reformer together with the tail gas feed for the steam reforming.

8. The method according to claim 4, wherein the natural gas or other fossil fuels is added to the steam reformer together with the tail gas feed for the steam reforming.

9. The method according to claim 1, wherein the reformed tail gas is introduced into the gas stream after the reacting but prior to the passing.

10. The method according to claim 2, wherein the reformed tail gas is introduced into the gas stream after the reacting but prior to the passing.

11. The method according to claim 4, wherein the reformed tail gas is introduced into the gas stream after the reacting but prior to the passing.

12. The method according to claim 5, wherein the reformed tail gas is introduced into the gas stream after the reacting but prior to the passing.

13. The method according to claim 1, wherein the reformed tail gas is introduced into the gas stream before the reacting.

14. The method according to claim 2, wherein the reformed tail gas is introduced into the gas stream before the reacting.

15. The method according to claim 4, wherein the reformed tail gas is introduced into the gas stream before the reacting.

16. The method according to claim 5, wherein the reformed tail gas is introduced into the gas stream before the reacting.

17. The method according to claim 1, wherein a portion of the reformed tail gas is introduced into the gas stream before the reacting, and a portion of the reformed tail gas is introduced after the reacting but prior to the passing.

18. The method according to claim 2, wherein a portion of the reformed tail gas is introduced into the gas stream before the reacting, and a portion of the reformed tail gas is introduced after the reacting but prior to the passing.

19. The method according to claim 4, wherein a portion of the reformed tail gas is introduced into the gas stream before the reacting, and a portion of the reformed tail gas is introduced after the reacting but prior to the passing.

20. The method according to claim 5, wherein a portion of the reformed tail gas is introduced into the gas stream before the reacting, and a portion of the reformed tail gas is introduced after the reacting but prior to the passing.

* * * * *

UNITED STATES PATENT AND TRADEMARK OFFICE
CERTIFICATE OF CORRECTION

PATENT NO. : 6,696,501 B2
DATED : February 24, 2004
INVENTOR(S) : Dag Schanke et al.

It is certified that error appears in the above-identified patent and that said Letters Patent is hereby corrected as shown below:

Column 1,
Line 65, "5)" should be moved from the right side of the column to the left side of the column.

Column 6,
Line 65, delete "28" and insert -- 20 --.

Column 7,
Line 2, delete "28" and insert -- 20 --.

Column 7, line 51-Column 8, Line 24,
Insert Ex. F as follows:

| Ex. F |
|---|
| 7440 |
| 0.6 |
| 3617 |
| 30 |
| 9 |
| 61 |
| 0.74 |
| 0.86 |
| 800 |
| 74.1 |
| 62.1 |
| 109.1 |

UNITED STATES PATENT AND TRADEMARK OFFICE
CERTIFICATE OF CORRECTION

PATENT NO. : 6,696,501 B2
DATED : February 24, 2004
INVENTOR(S) : Dag Schanke et al.

It is certified that error appears in the above-identified patent and that said Letters Patent is hereby corrected as shown below:

Column 9,
Line 4, after "stream", insert -- mainly --.
Line 6, delete "reformer" and insert -- reformer; --.
Line 8, delete "reacter." and insert -- reactor. --.
.

Signed and Sealed this

Twenty-fifth Day of May, 2004

JON W. DUDAS
*Acting Director of the United States Patent and Trademark Office*